United States Patent [19]
Edwards

[11] Patent Number: 5,707,349
[45] Date of Patent: Jan. 13, 1998

[54] METHOD FOR TREATMENT OF AIR WAY OBSTRUCTIONS

[75] Inventor: Stuart D. Edwards, Los Altos, Calif.

[73] Assignee: Somnus Medical Technologies, Inc., Sunnyvale, Calif.

[21] Appl. No.: 606,195

[22] Filed: Feb. 23, 1996

Related U.S. Application Data

[63] Continuation-in-part of Ser. No. 516,781, Aug. 18, 1995, which is a continuation-in-part of Ser. No. 239,658, May 9, 1994, Pat. No. 5,456,662.

[51] Int. Cl.$^6$ .................................................. A61B 17/39
[52] U.S. Cl. ............................................................ 604/22
[58] Field of Search .......................... 606/27–34, 37–42, 606/45–52, 110, 111; 604/21, 22; 607/96–102, 134, 135, 154, 156

Primary Examiner—Michael Powell Buiz
Assistant Examiner—Manuel Mendez
Attorney, Agent, or Firm—Wilson Sonsini Goodrich & Rosati

[57] ABSTRACT

A method for debulking the tongue provides an ablation apparatus including a source of electromagnetic energy and one or more electromagnetic energy delivery electrodes coupled to the electromagnetic energy source. At least one electrode is advanced into an interior of the tongue. Electromagnetic energy is delivered from the electrode to debulk an interior section of the tongue without damaging a hypoglossal nerve. The electrode is then retracted from the interior of the tongue.

42 Claims, 12 Drawing Sheets

METHOD FOR TREATMENT OF AIR WAY OBSTRUCTIONS

CROSS-REFERENCE TO RELATED APPLICATIONS

This application is a continuation in part of U.S. patent application Ser. No. 08/516,781 filed Aug. 18, 1995 and still pending, entitled "Ablation Apparatus and System for Removal of Soft Palate Tissue", having named inventors Stuart D. Edwards, Edward J. Gough and David L. Douglass, which is a continuation-in-part of U.S. application Ser. No. 08/239,658, filed May 9, 1994 entitled "Method for Reducing Snoring by RF Ablation of the Uvula" and now U.S. Pat. No. 5,456,662. Both applications are assigned to the assignee of the instant application and are herein incorporated by reference.

BACKGROUND OF THE INVENTION

1. Field of the Invention

This invention relates to a method for maintaining upper airway patency in human patients, and more particularly to a method which utilizes electromagnetic energy to debulk selected sections of the tongue and/or lingual tonsil without damaging the hypoglossal nerve.

2. Description of Related Art

Sleep-apnea syndrome is a medical condition characterized by daytime hypersomnomulence, morning arm aches, intellectual deterioration, cardiac arrhythmias, snoring and thrashing during sleep. It is caused by frequent episodes of apnea during the patient's sleep. The syndrome is classically subdivided into two types. One type, termed "central sleep apnea syndrome", is characterized by repeated loss of respiratory effort. The second type, termed obstructive sleep apnea syndrome, is characterized by repeated apneic episodes during sleep resulting from obstruction of the patient's upper airway or that portion of the patient's respiratory tract which is cephalad to, and does not include, the larynx.

Treatment thus far includes various medical, surgical and physical measures. Medical measures include the use of medications such as protriptyline, medroxyprogesterone, acetazolamide, theophylline, nicotine and other medications in addition to avoidance of central nervous system depressants such as sedatives or alcohol. The medical measures above are sometimes helpful but are rarely completely effective. Further, the medications frequently have undesirable side effects.

Surgical interventions have included uvulopalatopharyngoplasty, tonsillectomy, surgery to correct severe retrognathia and tracheostomy. In one procedure the jaw is dislodged and pulled forward, in order to gain access to the base of the tongue. These procedures may be effective but the risk of surgery in these patients can be prohibitive and the procedures are often unacceptable to the patients.

Physical measures have included weight loss, nasopharyngeal airways, nasal CPAP and various tongue retaining devices used nocturnally. These measures may be partially effective but are cumbersome, uncomfortable and patients often will not continue to use these for prolonged periods of time. Weight loss may be effective but is rarely achieved by these patients.

In patients with central sleep apnea syndrome, phrenic nerve or diaphragmatic pacing has been used. Phrenic nerve or diaphragmatic pacing includes the use of electrical stimulation to regulate and control the patient's diaphragm which is innervated bilaterally by the phrenic nerves to assist or support ventilation. This pacing is disclosed in *Direct Diaphragm Stimulation* by J. Mugica et al. PACE vol. 10 January-February 1987, Part II, *Preliminary Test of a Muscular Diaphragm Pacing System on Human Patients* by J. Mugica et al. from Neurostimulation: An Overview 1985 pp. 263–279 and *Electrical Activation of Respiration* by Nochomovitez IEEE Eng. in Medicine and Biology; June, 1993.

However, it was found that many of these patients also have some degree of obstructive sleep apnea which worsens when the inspiratory force is augmented by the pacer. The ventilation induced by the activation of the diaphragm also collapses the upper airway upon inspiration and draws the patient's tongue inferiorly down the throat choking the patient. These patients then require tracheostomies for adequate treatment.

A physiological laryngeal pacemaker as described in *Physiological Laryngeal Pacemaker* by F. Kaneko et al. from Trans Am Soc Artif Intern Organs 1985 senses volume displaced by the lungs and stimulates the appropriate nerve to open the patient's glottis to treat dyspnea. This apparatus is not effective for treatment of sleep apnea. The apparatus produces a signal proportional in the displaced air volume of the lungs and thereby the signal produced is too late to be used as an indicator for the treatment of sleep apnea. There is often no displaced air volume in sleep apnea due to obstruction.

One measure that is effective in obstructive sleep apnea is tracheostomy. However, this surgical intervention carries considerable morbidity and is aesthetically unacceptable to many patients. Other surgical procedures include pulling the tongue as forward as possible and surgically cutting and removing sections of the tongue and other structures which can close off the upper airway passage.

There is a need for a method to treat airway obstruction disorders that decreases the volume of portions of the tongue without damaging the hypoglossal nerve and with reduced surgical intervention.

SUMMARY OF THE INVENTION

Accordingly, an object of the invention is to provide a method that reduces the volume of selected portions of the tongue without damaging the hypoglossal nerve and with reduced surgical intervention.

Another object of the invention is to provide a method that provides sufficient electromagnetic energy to debulk the tongue without damaging the hypoglossal nerve.

A further object of the invention is to provide a method that provides sufficient electromagnetic energy to debulk the tongue without damaging the hypoglossal nerve resulting in a larger airway passage.

Yet another object of the invention is to provide a method for treating airway obstructions by debulking the tongue.

Another object of the invention is to provide a method for treating airway obstructions by debulking the lingual tonsil.

These and other objects of the invention are achieved by providing an ablation apparatus including a source of electromagnetic energy and one or more electromagnetic energy delivery electrodes coupled to the energy source. At least one electrode is advanced into an interior of the tongue. Electromagnetic energy is delivered from the electrode to debulk a section of the tongue without damaging a hypoglossal nerve. The electrode is then removed from the interior of the tongue.

One method for treating airway obstructions is achieved by debulking one or more interior sections of the tongue.

This provides a larger airway passage. Another method for treating airway obstructions is achieved by debulking sections of the lingual tonsil.

The electromagnetic energy source can be any source of energy that can provide the bulking including but not limited to RF, microwave and the like.

In one embodiment, at least one electrode is introduced into the tongue and at least 1% of the tongue is debulked. Electrodes can be introduced from the tip of the tongue, and/or the dorsal or ventral surfaces. One or more electrodes can be advanced into through different surfaces of the tongue such as the tip, the ventral surface, the dorsum of the tongue or the interior dorsal surface.

In one embodiment, a catheter is provided with a lumen and the electrodes are advanced out of the catheter and into an interior of the tongue. The catheter is malleable in order to conform to a the surface of a patient's tongue. Further, a distal end of the catheter can be deflectable.

The catheter can include a cooling element, including but not limited to a cooling channel coupled to a source of cooling medium. Optionally provided is an imaging apparatus such as an ultrasound apparatus.

DETAILED DESCRIPTION

A method for debulking the tongue, lingual tonsil and/or adenoids provides an ablation apparatus including a source of electromagnetic energy and one or more electromagnetic energy delivery electrodes coupled to the electromagnetic energy source. At least one electrode is advanced into an interior of the tongue. Sufficient electromagnetic energy is delivered from the electrode to debulk a section of the tongue without damaging the hypoglossal nerve. The electrode is then removed from the interior of the tongue. A method for treating airway obstructions is achieved by debulking the tongue without damaging the hypoglossal nerve. The electrode can be introduced into the tongue from the tongue's tip, ventral surface, dorsum, underneath the tongue, along the tongue's midline, or in certain instances through the chin area. The tongue is ablated (debulked) without damaging the hypoglossal nerves. This is achieved by positioning the electrodes far enough away from the hypoglossal nerves so that during the delivery of electromagnetic energy to the tongue, the hypoglossal nerves are not damaged. Another method for treating airway obstructions is achieved by debulking the lingual tonsil without damaging the hypoglossal nerve. These methods are used to treat sleep apnea.

Figure 1:
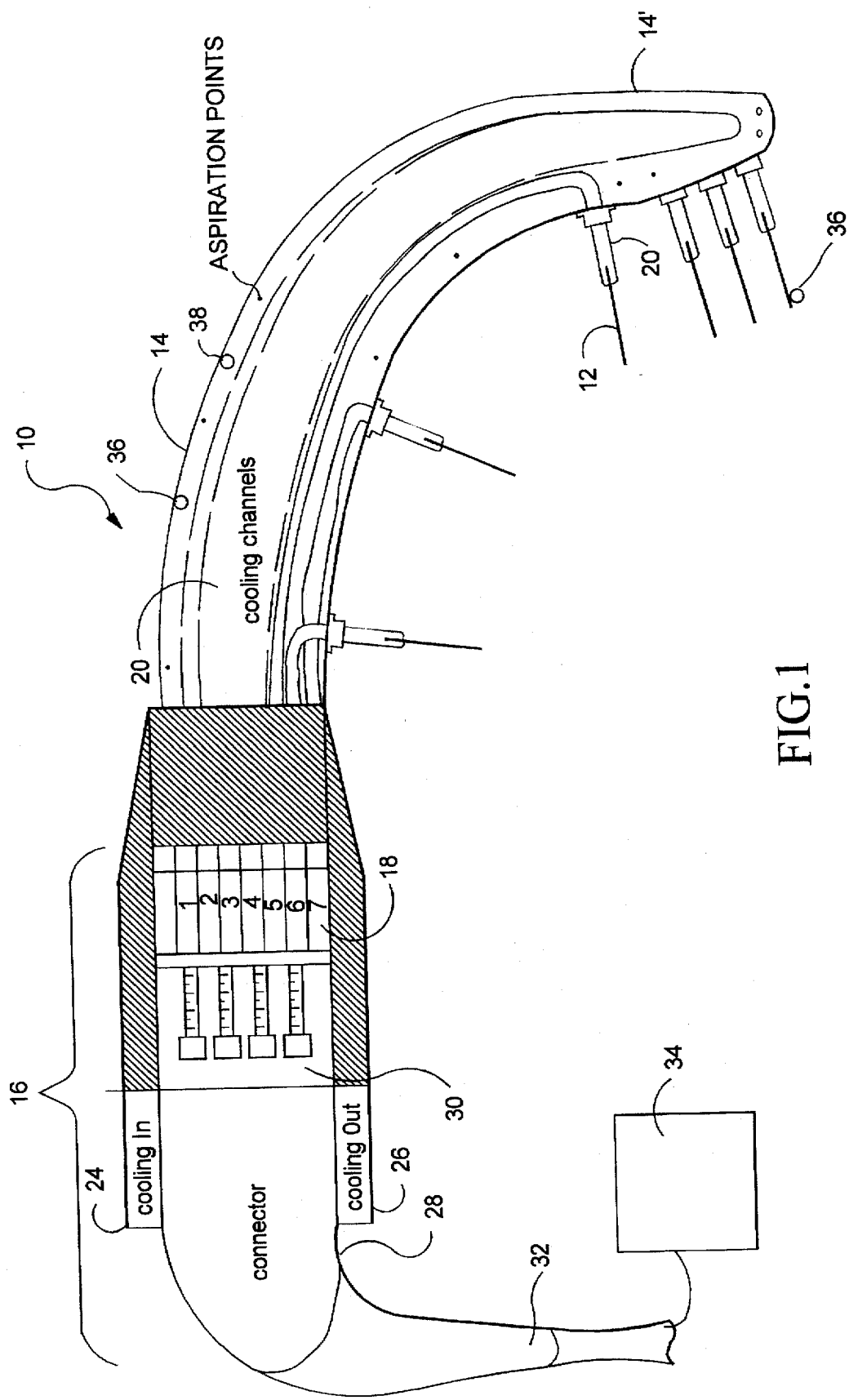
FIG. 1 is a cross-sectional view of an ablation apparatus used with the methods of the present invention.
Figure 2:
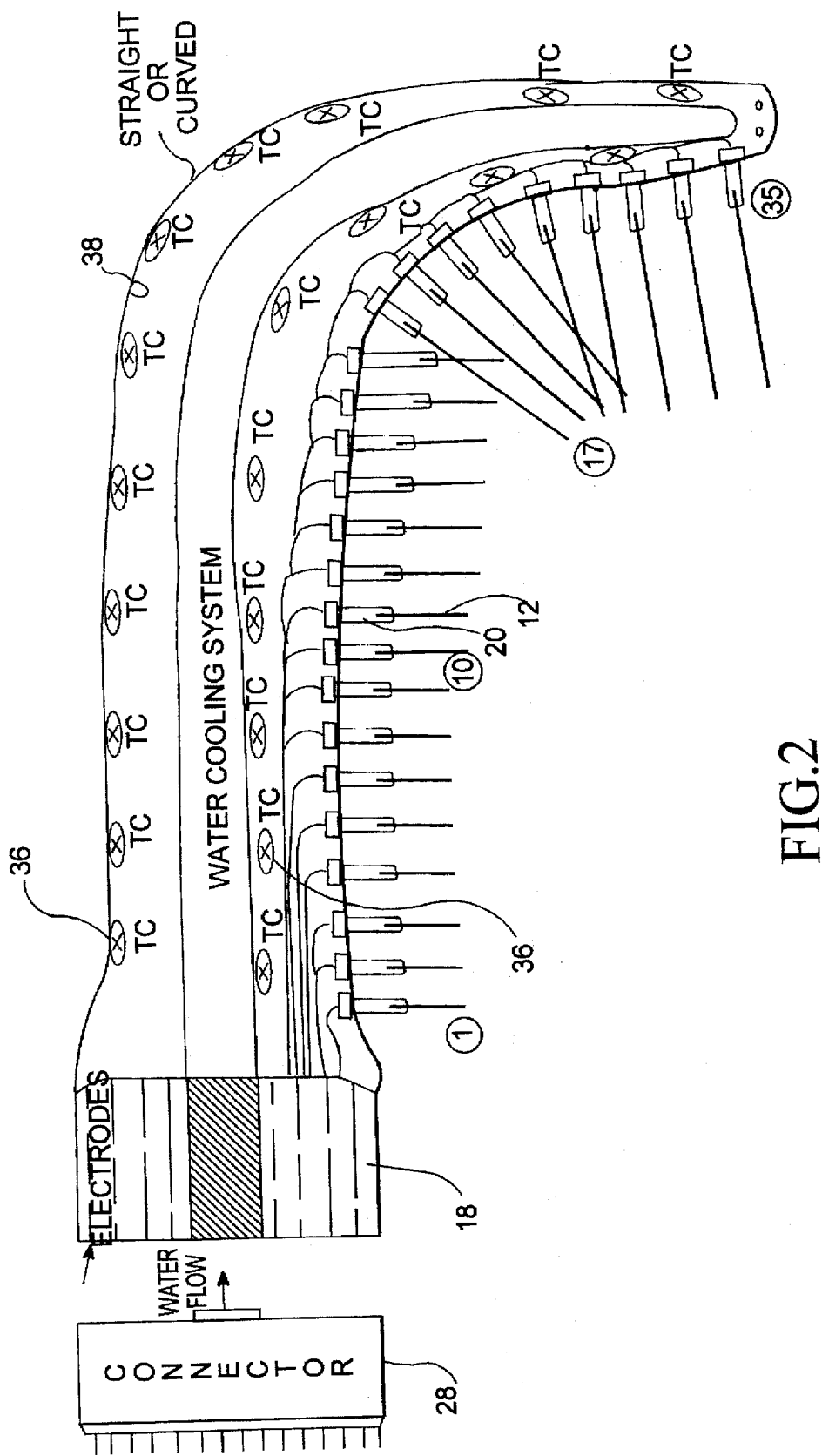
FIG. 2 is cross-sectional view illustrating the catheter and connector of the ablation apparatus shown in FIG. 1.

Referring to FIGS. 1 and 2, an ablation apparatus 10 for debulking the tongue, lingual tonsils, and/or adenoids is illustrated. Ablation apparatus 10 can be positioned so that one or more electrodes 12 are introduced into an interior of the tongue through the tongue. Ablation apparatus 10 may include atraumatic intubation with or without visualization, provide for the delivery of oxygen or anesthetics, and can be capable of suctioning blood or other secretions. It will be appreciated that ablation apparatus 10 is used to treat a variety of different obstructions in the body where passage of gas is restricted. One embodiment is the treatment of sleep apnea using electrodes 12 to ablate selected portions of the tongue, lingual tonsils and/or adenoids by the use of RF, microwave, and the like. In this regard, ablation apparatus 10 can be used to ablate targeted masses including but not limited to the tongue, tonsils, turbinates, soft palate tissues, hard tissue and mucosal tissue. In one embodiment, ablation apparatus 10 is used to debulk the tongue in order to increase the cross-sectional area of the air passageway.

Prior to debulking the tongue, a presurgical evaluation may be performed including a physical examination, fiberoptic pharyngoscopy, cephalometric analysis and polygraphic monitoring. The physical examination emphasizes the evaluation of the head and neck. It also includes a close examination of the nasal cavity to identify obstructing deformities of the septum and turbinate; oropharyngeal obstruction from a long, redundant soft palate or hypertrophic tonsils; and hypopharyngeal obstruction from a prominent base of the tongue.

Ablation apparatus 10 includes a catheter 14, a handle 16, one or more electrodes 12 extending from different ports formed along a longitudinal surface of catheter 14 or from its distal end, as well as an electrode advancement and retraction device 18.

Electrodes 12 can include a central lumen for receiving a variety of fluids that can be introduced into the interior of the tongue, as well as a plurality of fluid delivery ports. One suitable fluid is an electrolytic solution. Instead of direct contact with tissue and electrode 12 for the delivery of thermal energy, a cooled electrolytic solution can be used to deliver the thermal energy to the tissue. The electrolytic solution may be cooled in the range of about 30 to 55 degrees C.

Figure 3:
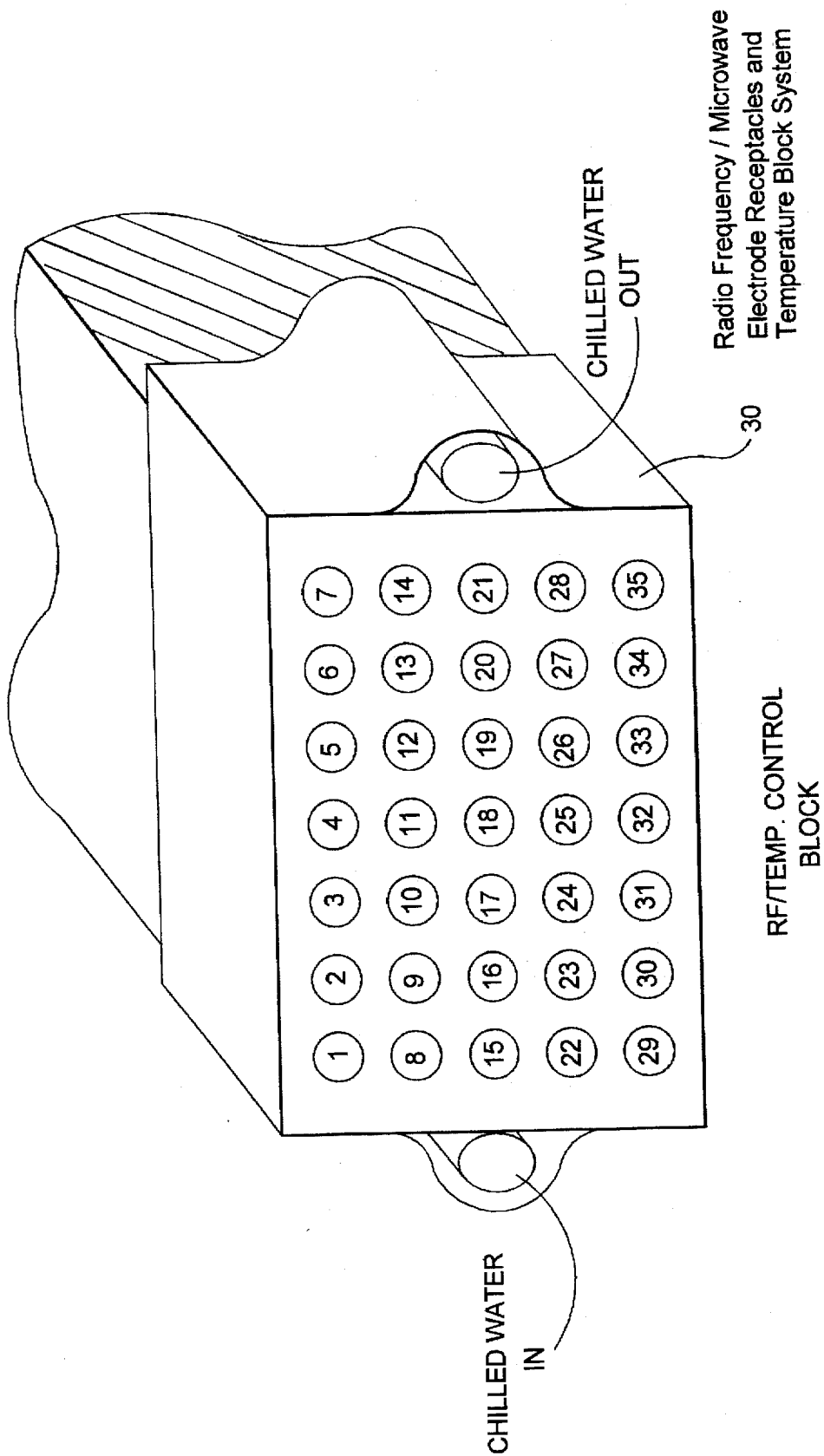
FIG. 3 is a perspective view of the connector illustrated in FIG. 1.
Figure 5:
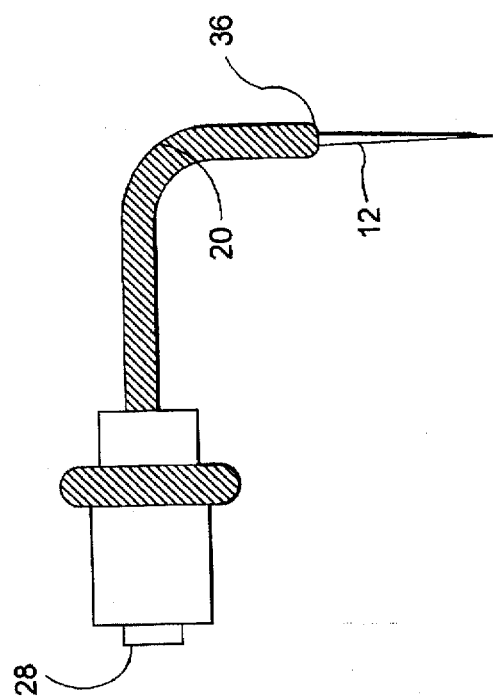
FIG. 5 is a perspective view of a flexible needle electrode utilized with the methods of the present invention.
Figure 4:
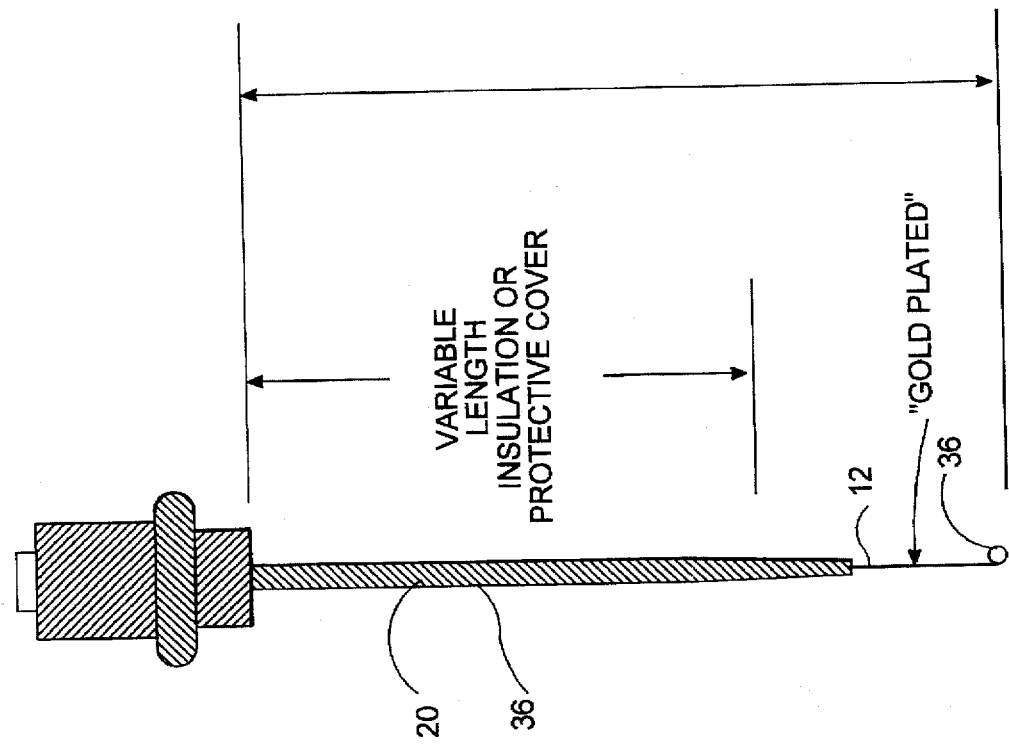
FIG. 4 is a perspective view of a needle electrode associated with the ablation apparatus illustrated in FIG. 1.

An electromagnetic energy delivery surface of electrode 12 can be adjusted by the inclusion of an adjustable or non-adjustable insulation sleeve 20 (FIGS. 3 and 4). Insulation sleeve 20 can be advanced and retracted along the exterior surface of electrode 12 in order to increase or decrease the length of the electromagnetic energy delivery surface of electrode 12. Insulation sleeve 20 can be made of a variety of materials including but not limited to nylon, polyimides, other thermoplastics and the like. The amount of available electromagnetic energy delivery surface of electrode 12 can be varied by other methods including but not limited to creating a segmented electrode with a plurality of electrodes that are capable of being multiplexed and individually activated, and the like.

Handle 12 is preferably made of an insulating material. Examples of such suitable insulating materials include but are not limited to stainless steel, platinum, other noble metals and the like. Electrodes 12 are made of a conductive material such as stainless steel. Additionally, electrodes 12 can be made of a shaped memory metal, such as nickel titanium, commercially available from Raychem Corporation, Menlo Park, Calif. It is possible that only a distal end of electrode 12 is made of the shaped memory metal in order to effect a desired deflection.

For many applications it is desirable for a distal end 14' of catheter 14 to be deflectable. This can be achieved mechanically or with the use of memory metals. A steering wire, or other mechanical structure, can be attached to either the exterior or interior of distal end 14'. In one embodiment, a deflection knob located on handle 16 is activated by the physician causing a steering wire to tighten. This imparts a retraction of distal end 14', resulting in its deflection. It will be appreciated that other mechanical devices can be used in place of the steering wire. The deflection may be desirable for tissue sites with difficult access.

Catheter 14 can be malleable in order to conform to the surface of the tongue when a selected ablation target site is selected. An encapsulated soft metal, such as copper, or an annealed metal/plastic material can be used to form malleable catheter 14. All or a portion of catheter 14 may be malleable or made of a shaped memory metal.

Catheter 14 may include a cooling system, including but not limited to a cooling channel 22 with a cooling inlet 24 for receiving a cooling medium such as water, and a cooling outlet 26. Other methods for cooling are suitable, including but not limited to a cooling channel on an exterior surface of catheter 14. Cooling is desirable to minimize adhesion of catheter 14 to the tongue, reduce the risk of an edemanous response of the tongue and other body organs or structures, and control the temperature of the ablation.

Handle 12 can comprise a connector 28 coupled to retraction and advancement device 18. Connector 28 provides a coupling of electrodes 12 to power, feedback control, temperature and/or imaging systems. An RF/temperature control block 30 can be included.

In one embodiment, the physician moves retraction and advancement device 18 in a direction toward a distal end of connector 28. Electrodes 12 can be spring loaded. When retraction and advancement device is moved back, springs cause selected electrodes 12 to advance out of catheter 14. Electrodes 12 can be deployed in a lateral direction relative to a longitudinal axis of catheter 14, out of catheter distal end 14', and the like.

One or more cables 32 couple electrodes 12 to an electromagnetic energy source 34. A variety of energy sources 34 can be used with the present invention to transfer thermal energy to the tissue site, including but not limited to RF, microwave, ultrasonic, coherent light and thermal transfer. Preferably, energy source 34 is an RF generator. When an RF energy source is used, the physician can activate RF energy source 34 by the use of a foot switch (not shown) coupled to RF energy source 34.

One or more sensors 36 may be positioned on an interior or exterior surface of antenna 12, insulation sleeve 20, or be independently inserted into the tissue site separably from ablation apparatus 10. Sensors 36 permit accurate measurement of temperature at a tissue site in order to determine, (i) the extent of ablation, (ii) the amount of ablation, (iii) whether or not further ablation is needed, and (iv) the boundary or periphery of the ablated geometry. Further, sensors 36 prevent non-targeted tissue from being destroyed or ablated.

Sensors 36 are of conventional design, including but not limited to thermistors, thermocouples, resistive wires, and the like. Suitable sensors 36 include a T type thermocouple with copper constantene, J type, E type, K type, fiber optics, resistive wires, thermocouple IR detectors, and the like. It will be appreciated that sensors 36 need not be thermal sensors.

Sensors 36 measure temperature and/or impedance to permit ablation monitoring. This reduces damage to tissue surrounding the targeted ablation mass. By monitoring the temperature at various points within the interior of the selected tissue mass the periphery of ablation can be ascertained and it is possible to determine when the ablation is completed. If at any time sensor 36 determines that a desired ablation temperature is exceeded, then an appropriate feedback signal is received at electromagnetic energy source 34 and the amount of energy delivered is regulated.

Ablation apparatus 10 can include visualization capability including but not limited to a viewing scope, an expanded eyepiece, fiber optics, video imaging, and the like.

Additionally, ultrasound imaging can be used to position the electrodes 12 and/or determine the amount of ablation. One or more ultrasound transducers 38 can be positioned in or on electrode 12 or catheter 14. An imaging probe may also be used internally or eternally to the selected tissue site. A suitable imaging probe is Model 21362, manufactured and sold by Hewlett Packard Company. Each ultrasound transducer 38 is coupled to an ultrasound source. In one embodiment, ultrasound transducer 38 is a piezoelectric crystal mounted on a backing material. The piezoelectric crystal is connected by electrical leads to the ultrasound source. Ultrasound transducers 38 transmit ultrasound energy into adjacent tissue, including but not limited to the tongue.

Figure 6:
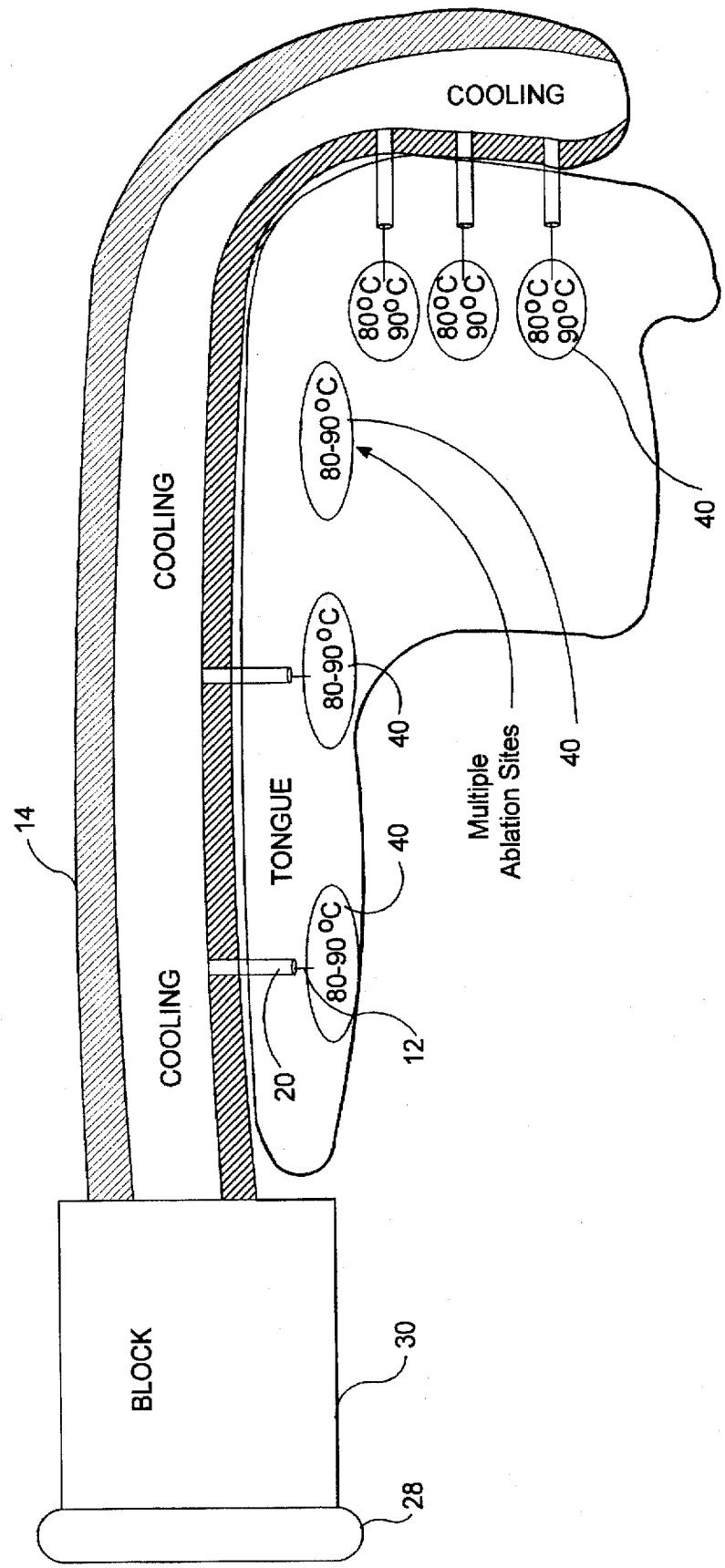
FIG. 6 illustrates the creation of ablation zones with the ablation apparatus shown in FIG. 1.
Figure 8:
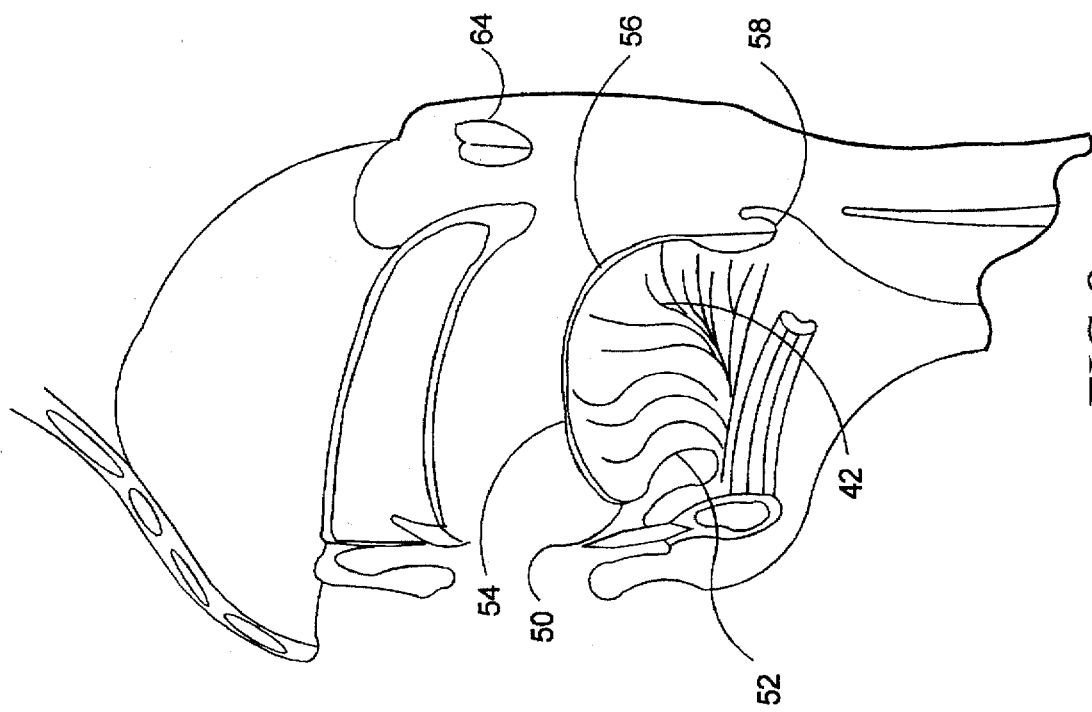
FIG. 8 is a cross-sectional view of the tongue with the mouth open.
Figure 7:
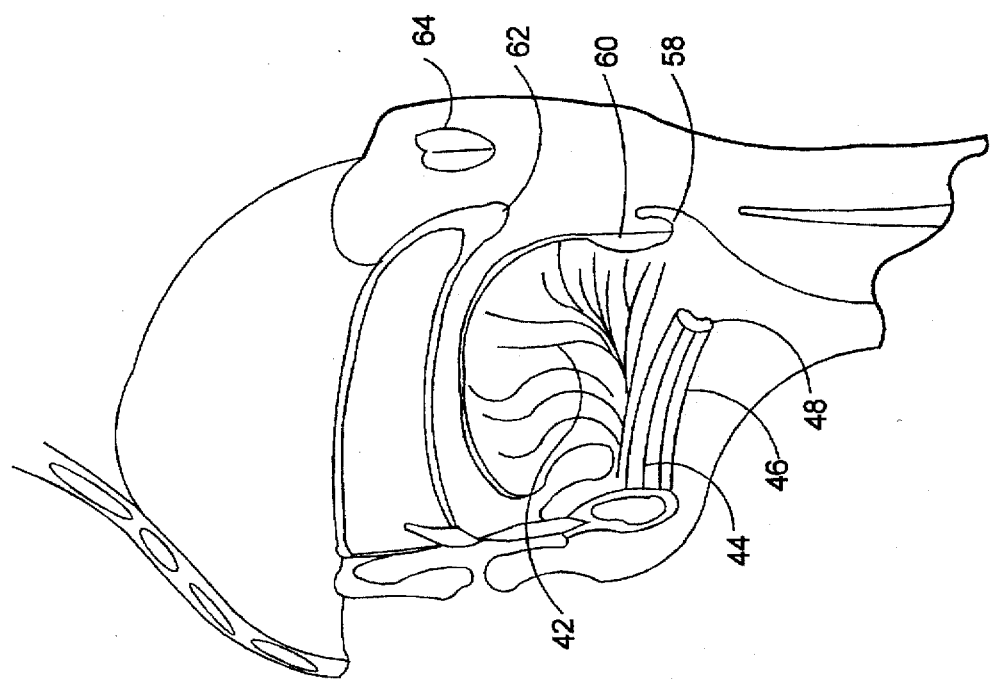
FIG. 7 is a cross-sectional view of the tongue with the mouth closed.
Figure 9:
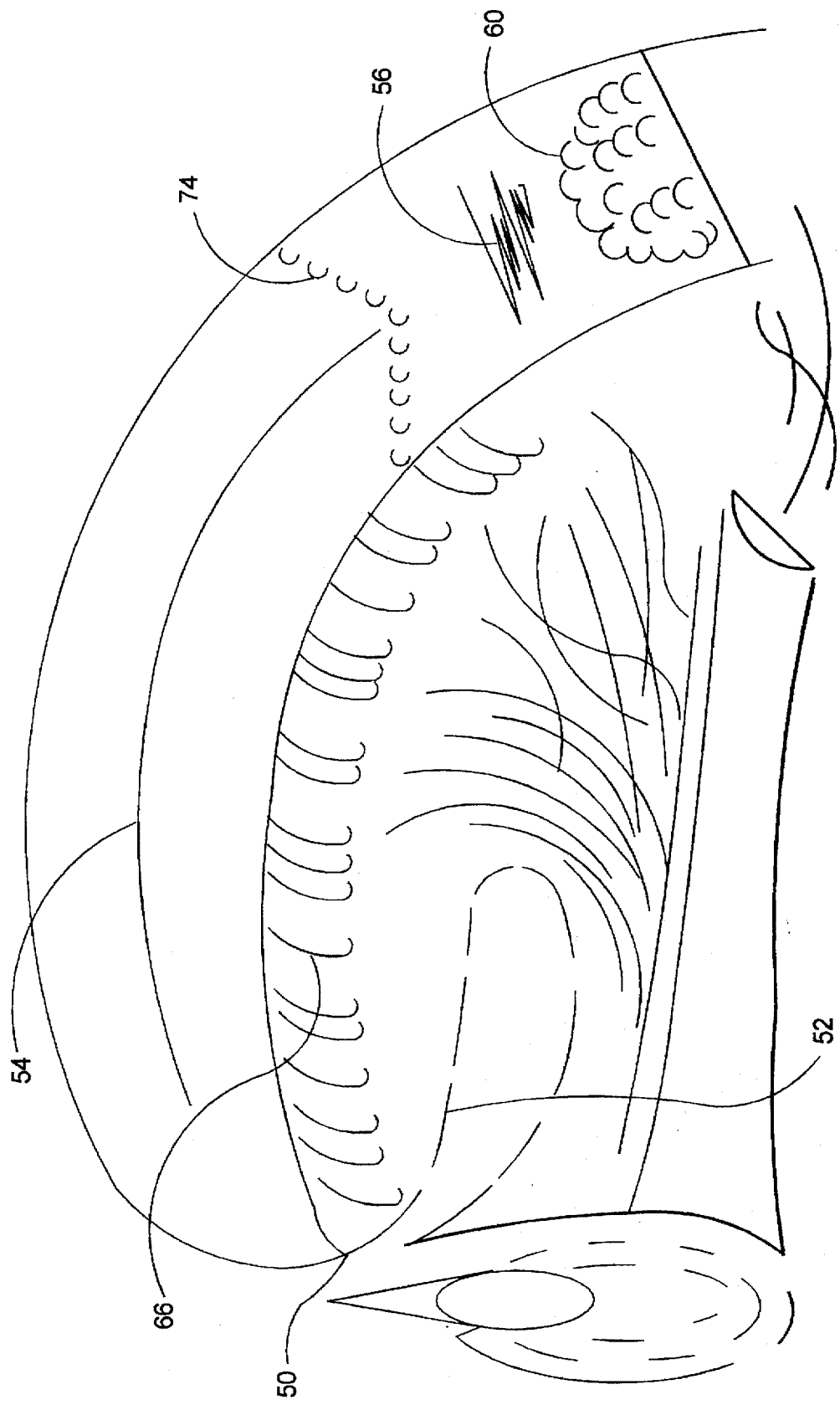
FIG. 9 is a perspective view of the tongue.
Figure 11:
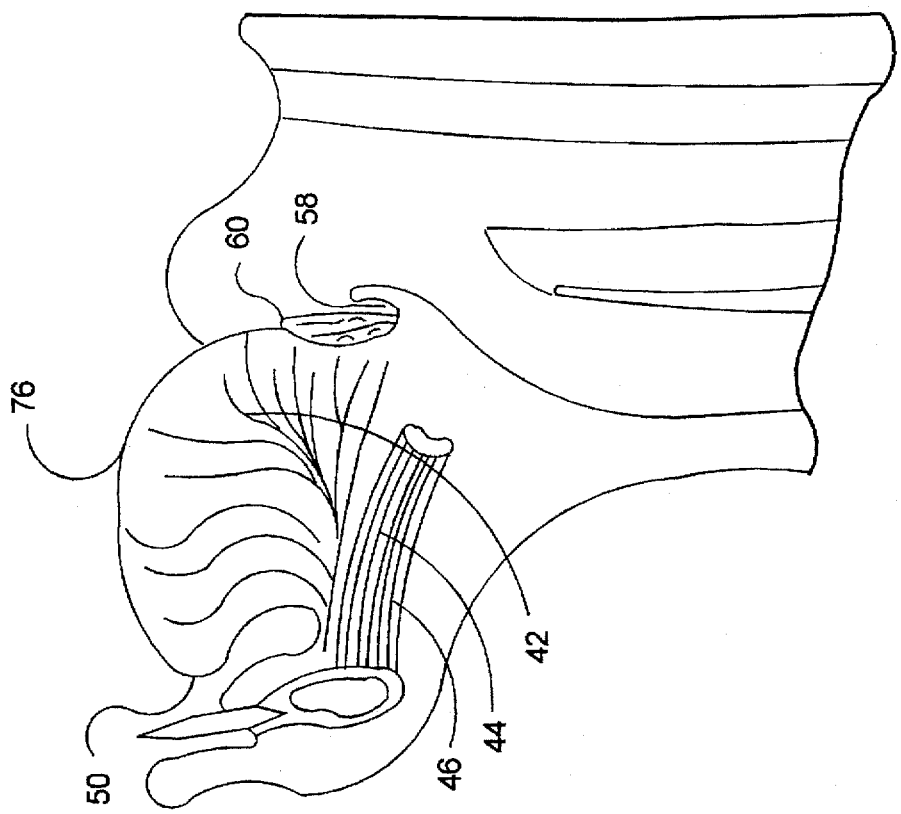
FIG. 11 is a cross-sectional view of the tongue.
Figure 10:
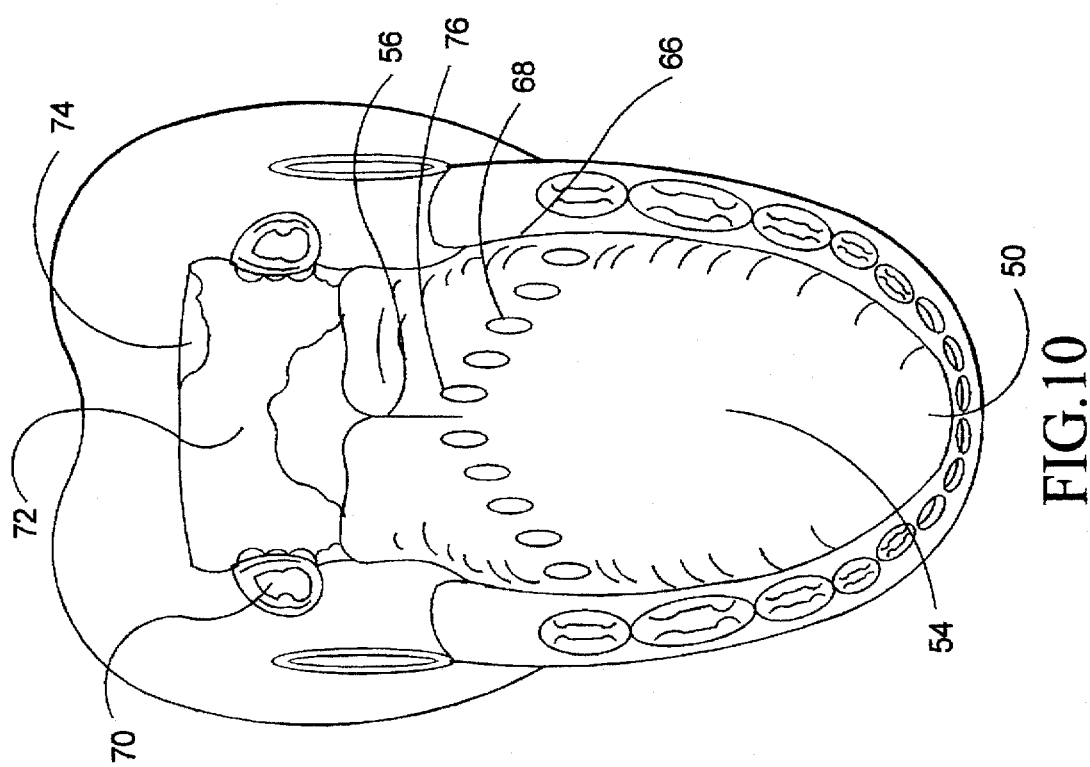
FIG. 10 is a perspective view of the dorsum of the tongue.
Figure 13:
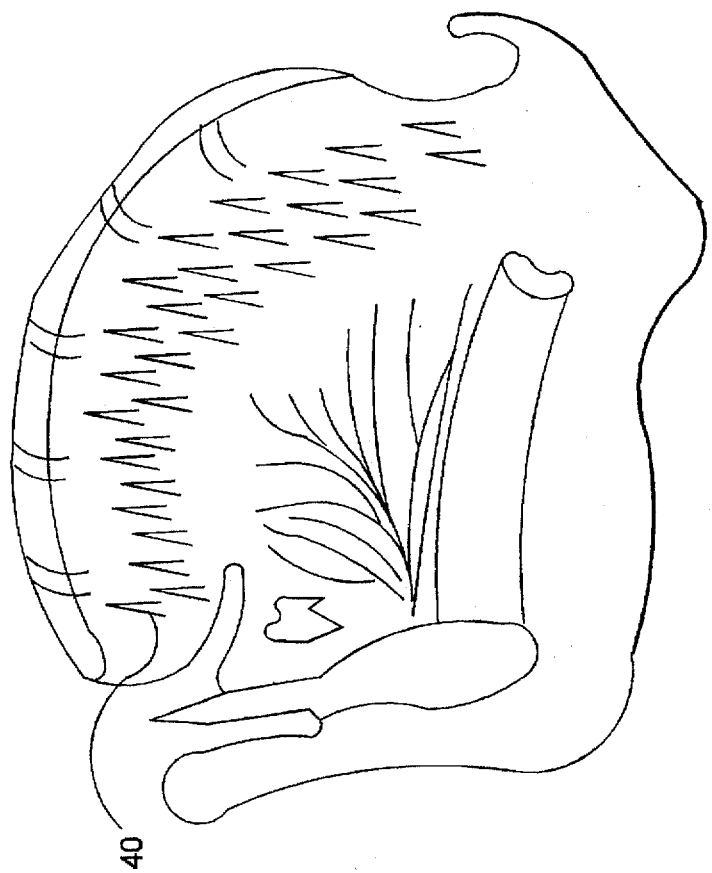
FIG. 13 is a cross-sectional view of the tongue illustrating a plurality of ablation zones.
Figure 12:
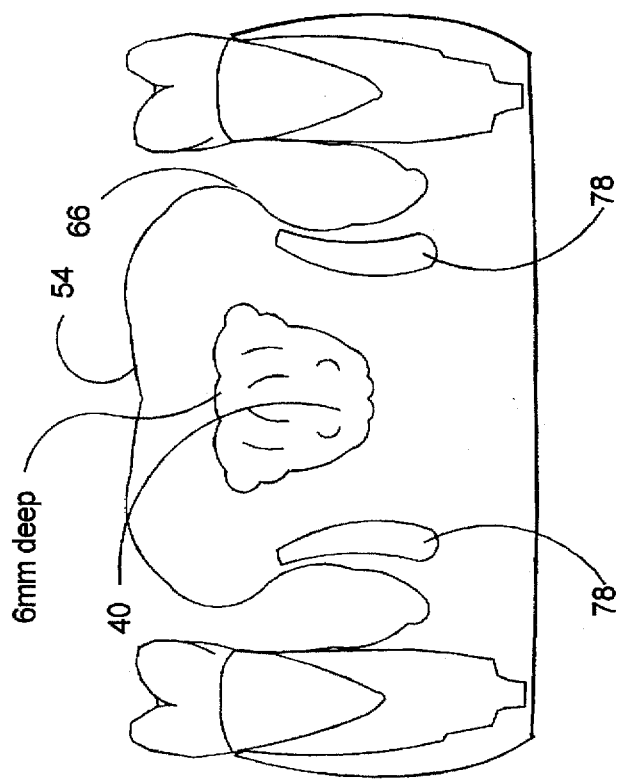
FIG. 12 is a cross-sectional view of the tongue illustrating the location of the hypoglossal nerves and the creation of an ablation zone.
Figure 15:
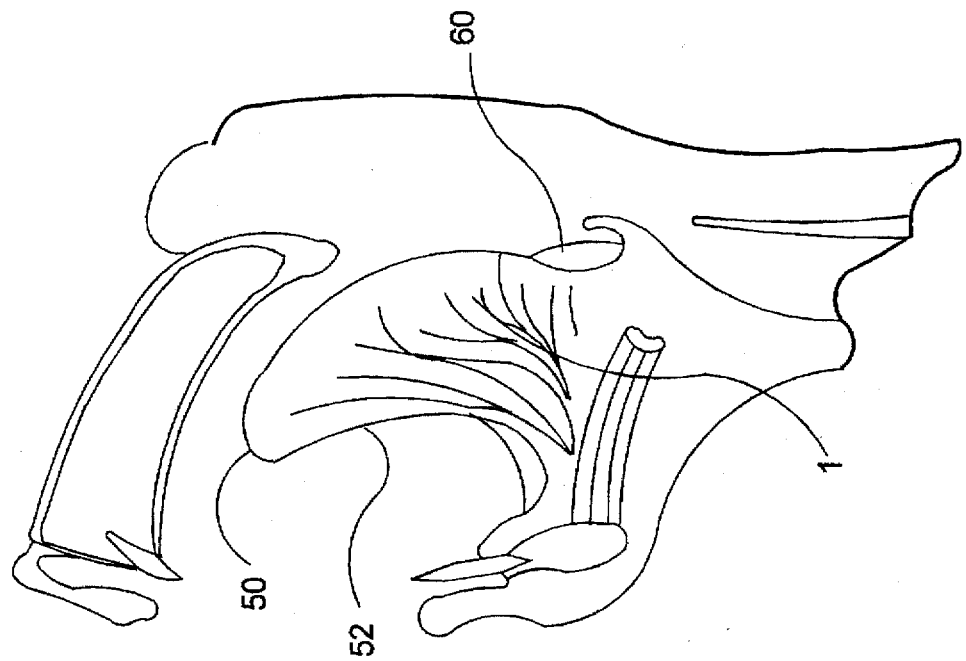
FIG. 15 is a cross-sectional view of the tongue.
Figure 14:
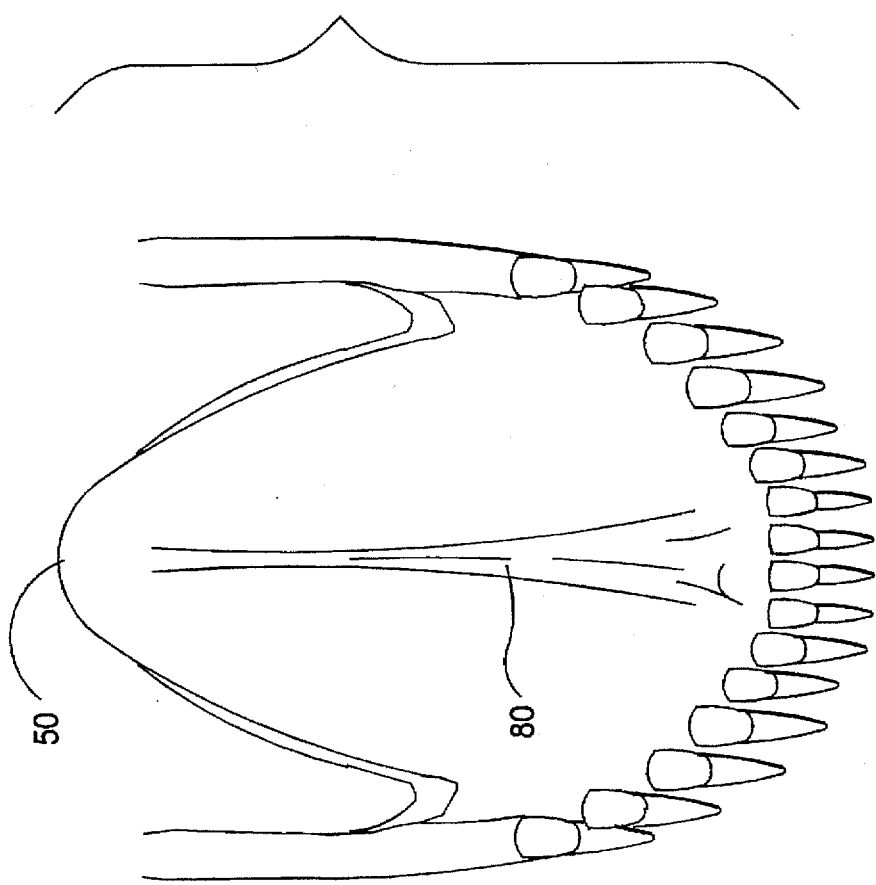
FIG. 14 is a perspective view of the ventral surface of the tongue.

With reference now to FIG. 6 catheter 14 is shown as being introduced into the oral cavity and multiple electrodes 12 are advanced into the interior of the tongue creating different ablation zones 40. Ablation apparatus can be operated in either bipolar or monopolar modes. In FIG. 6, electrodes 12 are operated in the bipolar mode, creating sufficient ablation zones 40 to debulk the tongue without affecting the hypoglossal nerves and creating a larger air passageway. With this debulking, the back of the tongue moves in a forward direction away from the air passageway. The result is an increase in the cross-sectional diameter of the air passageway.

Ablation apparatus 10 can also be operated in the monopolar mode. A groundpad can be positioned in a convenient place such as under the chin. A single electrode 12 is positioned in the tongue to create a first ablation zone 40. Electrode 12 can then be retracted from the interior of the tongue, catheter 14 moved, and electrode 12 is then advanced from catheter 14 into another interior section of the tongue. A second ablation zone 40 is created. This procedure can be completed any number of times to form different ablation regions in the interior of the tongue. More than one electrode 12 can be introduced into the tongue and operated in the bipolar mode. Electrodes 12 are then repositioned in the interior of the tongue any number of times to create a plurality of connecting or non-connecting ablation zones 40.

Referring now to FIGS. 7 through 15, various anatomical views of the tongue and other structures are illustrated. The different anatomical structures are as follows: the genioglossus muscle, or body of the tongue is denoted as 42; the geniohyoid muscle is 44; the mylohyoid muscle is 46; the hyoid bone is 48; the tip of the tongue is 50; the ventral surface of tongue 42 is denoted as 52; the dorsum of the tongue is denoted as 54; the dorsum of the tongue is denoted as 54; the inferior dorsal of the tongue is denoted as 56; the reflex of the vallecula is 58; the lingual follicles are denoted as 60; the uvula is 62; the adenoid area is 64; the lateral border of the tongue is 66; the circumvallate papilla is 68, the palatine tonsil is 70; the pharynx is 72; the redundant pharyngeal tissue is 74; the foramen cecum is 76; the hypoglossal nerve is 78, and the lingual frenum of the tongue is 80.

Dorsum 54 is divided into anterior 2/3 and inferior dorsal 56. The delineation is determined by circumvallate papilla 68 and foramen cecum 76. Inferior dorsal 56 is the dorsal surface inferior to circumvallate papilla 68 and superior reflex of the vallecula 58. Reflex of the vallecula 58 is the deepest portion of the surface of the tongue contiguous with the epiglottis. Lingual follicles 60 comprise the lingual tonsil.

Catheter 14 can be introduced through the nose or through the oral cavity. Electrodes 12 can be inserted into an interior of tongue 42 through dorsum surface 54, inferior dorsal surface 56, ventral surface 52, tip 50 or geniohyoid muscle 44. Additionally, electrodes may be introduced into an interior of lingual follicles 60 and into adenoid area 64. Once electrodes 12 are positioned, insulation sleeve 20 may be adjusted to provided a desired electromagnetic energy delivery surface for each electrode 12.

Ablation zones 40 are created without damaging hypoglossal nerves 78. This creates a larger air passageway and provides a treatment for sleep apnea.

In all instances, the positioning of electrodes 12, as well as the creation of the ablation zones is such that hypoglossal nerves 78 are not ablated or damaged. The ability to swallow and speak is not impaired.

Figure 16:
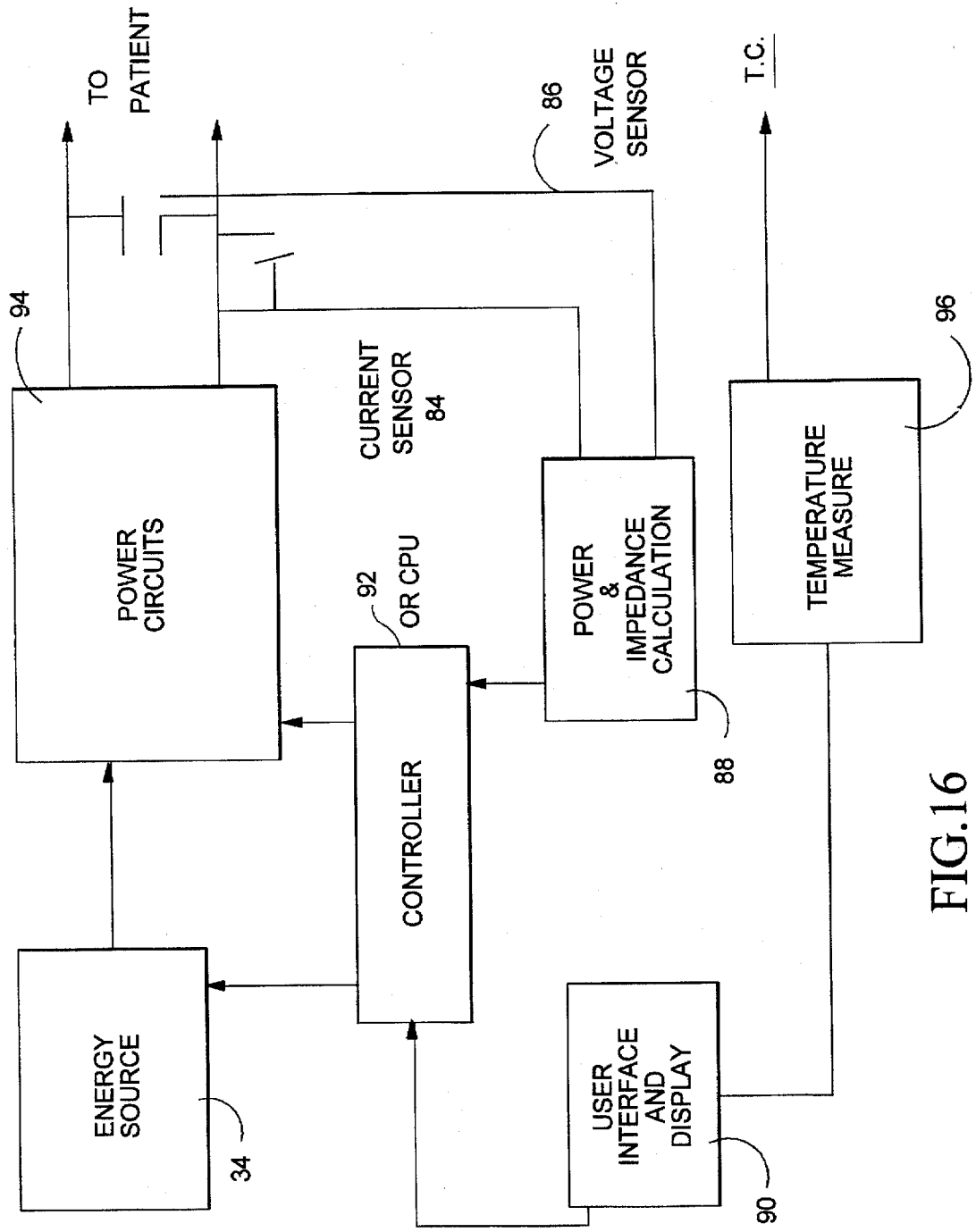
FIG. 16 is a block diagram of a feedback control system useful with the methods of the present invention.
Figure 17:
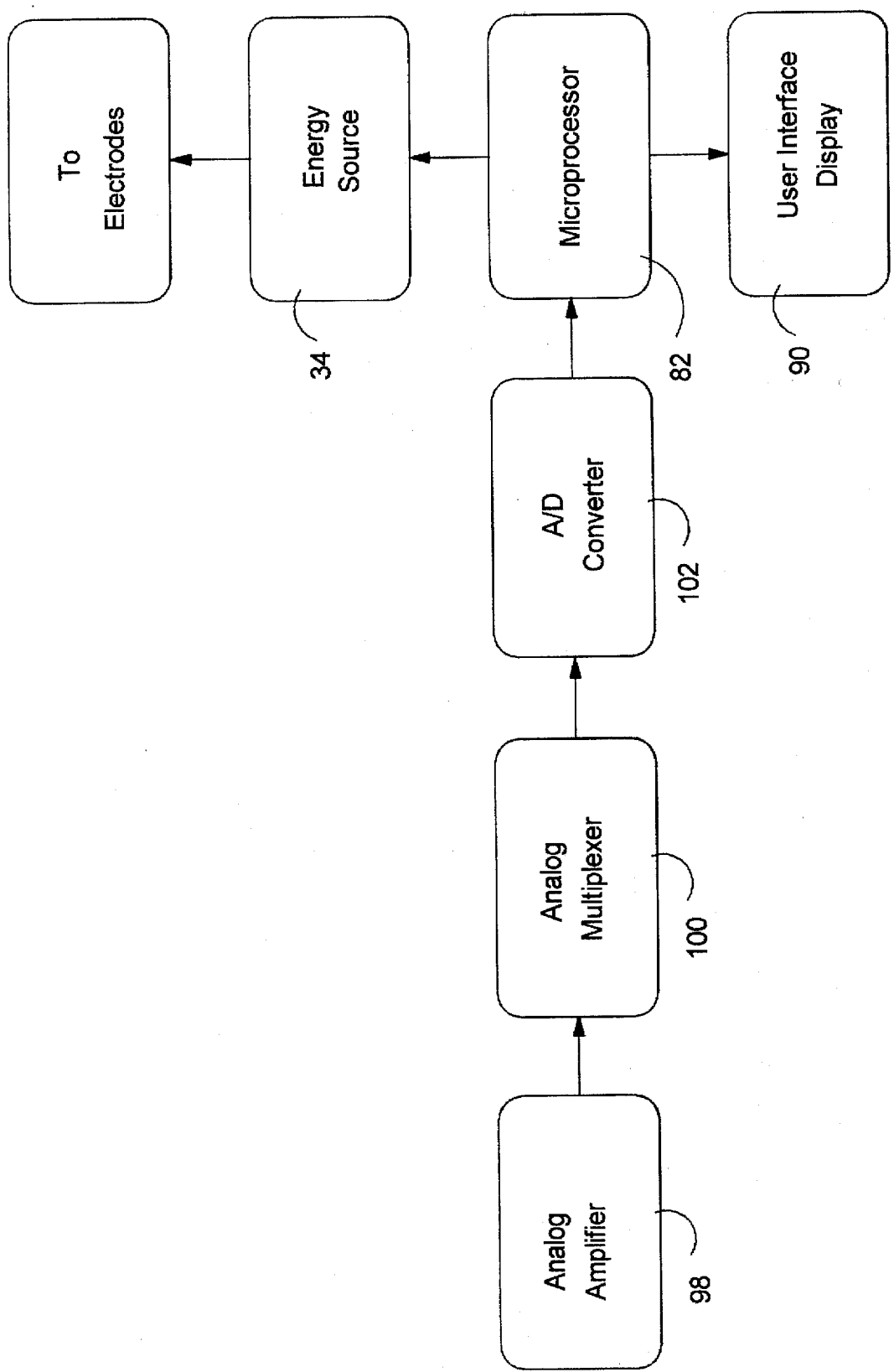
FIG. 17 is a block diagram illustrating an analog amplifier, analog multiplexer and microprocessor used with the feedback control system of FIG. 16.

Referring now to FIGS. 16 and 17 an open or closed loop feedback system couples sensors 36 to energy source 34. The temperature of the tissue, or of electrode 12 is monitored, and the output power of energy source 34 adjusted accordingly. The physician can, if desired, override the closed or open loop system. A microprocessor can be included and incorporated in the closed or open loop system to switch power on and off, as well as modulate the power. The closed loop system utilizes microprocessor 82 to serve as a controller, watch the temperature, adjust the RF power, look at the result, refeed the result, and then modulates the power.

With the use of sensors 36 and the feedback control system a tissue adjacent to RF electrodes 12 can be maintained at a desired temperature for a selected period of time without impeding out. Each RF electrode 12 is connected to resources which generate an independent output for each RF electrode 12. An output maintains a selected energy at RF electrodes 12 for a selected length of time.

Current delivered through RF electrodes 12 is measured by current sensor 84. Voltage is measured by voltage sensor 86. Impedance and power are then calculated at power and impedance calculation device 88. These values can then be displayed at user interface and display 90. Signals representative of power and impedance values are received by a controller 92.

A control signal is generated by controller 92 that is proportional to the difference between an actual measured value, and a desired value. The control signal is used by power circuits 94 to adjust the power output in an appropriate amount in order to maintain the desired power delivered at respective RF electrodes 12.

In a similar manner, temperatures detected at sensors 36 provide feedback for maintaining a selected power. The actual temperatures are measured at temperature measurement device 96, and the temperatures are displayed at user interface and display 90. A control signal is generated by controller 92 that is proportional to the difference between an actual measured temperature, and a desired temperature. The control signal is used by power circuits 94 to adjust the power output in an appropriate amount in order to maintain the desired temperature delivered at the respective sensor. A multiplexer can be included to measure current, voltage and temperature, at the numerous sensors 36, and energy can be delivered to RF electrodes 12 in monopolar or bipolar fashion.

Controller 92 can be a digital or analog controller, or a computer with software. When controller 92 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface and display 90 includes operator controls and a display. Controller 92 can be coupled to imaging systems, including but not limited to ultrasound, CT scanners, X-ray, MRI, mammographic X-ray and the like. Further, direct visualization and tactile imaging can be utilized.

The output of current sensor 84 and voltage sensor 86 is used by controller 92 to maintain a selected power level at RF electrodes 12. The amount of RF energy delivered controls the amount of power. A profile of power delivered can be incorporated in controller 92, and a preset amount of energy to be delivered can also be profiled.

Circuitry, software and feedback to controller 92 result in process control, and the maintenance of the selected power that is independent of changes in voltage or current, and are used to change, (i) the selected power, (ii) the duty cycle (on-off and wattage), (iii) bipolar or monopolar energy delivery, and (iv) infusion medium delivery, including flow rate and pressure. These process variables are controlled and varied, while maintaining the desired delivery of power independent of changes in voltage or current, based on temperatures monitored at sensors 36.

Current sensor 84 and voltage sensor 86 are connected to the input of an analog amplifier 98. Analog amplifier 98 can be a conventional differential amplifier circuit for use with sensors 36. The output of analog amplifier 98 is sequentially connected by an analog multiplexer 100 to the input of A/D converter 102. The output of analog amplifier 98 is a voltage which represents the respective sensed temperatures. Digitized amplifier output voltages are supplied by A/D converter 102 to microprocessor 82. Microprocessor 82 may be a type 68HCII available from Motorola. However, it will be appreciated that any suitable microprocessor or general purpose digital or analog computer can be used to calculate impedance or temperature.

Microprocessor 82 sequentially receives and stores digital representations of impedance and temperature. Each digital value received by microprocessor 82 corresponds to different temperatures and impedances.

Calculated power and impedance values can be indicated on user interface and display 90. Alternatively, or in addition to the numerical indication of power or impedance, calculated impedance and power values can be compared by microprocessor 82 with power and impedance limits. When the values exceed predetermined power or impedance values, a warning can be given on user interface and display 90, and additionally, the delivery of RF energy can be reduced, modified or interrupted. A control signal from microprocessor 82 can modify the power level supplied by energy source 34.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method for reducing a volume of a tongue, comprising:
   providing an ablation apparatus including a source of electromagnetic energy and one or more electromagnetic energy delivery electrodes coupled to the electromagnetic energy source;
   advancing at least one electrode into an interior of the tongue;
   delivering a sufficient amount of electromagnetic energy from the electrode into the interior of the tongue to debulk a section of the tongue without damaging the hypoglossal nerve; and
   retracting the electrode from the interior of the tongue.

2. The method of claim 1, wherein the energy source is an RF source.

3. The method of claim 1, wherein the energy source is a microwave source.

4. The method of claim 1, wherein the electrode is advanced into an interior of the tongue through a ventral surface of the tongue.

5. The method of claim 1, wherein the electrode is advanced into an interior of the tongue through an inferior dorsal surface of the tongue.

6. The method of claim 1, wherein the electrode is advanced into an interior of the tongue through a dorsum surface of the tongue.

7. The method of claim 1, wherein the electrode is advanced into an interior of the tongue through a tip of the tongue.

8. The method of claim 1, wherein two or more electrodes are advanced into a different interior area of the tongue.

9. The method of claim 1, wherein two or more electrodes are introduced through a different surface site of the tongue.

10. The method of claim 1, wherein the ablation apparatus further comprises:
    a catheter including a lumen, wherein the electrode is deployed from the catheter lumen into an interior of the tongue.

11. The method of claim 1, wherein the catheter further comprises:
    a cooling element.

12. The method of claim 11, wherein the cooling element comprises a cooling channel in an interior of the catheter, the cooling channel receiving a cooling medium and circulating the cooling medium through the interior of the catheter.

13. The method of claim 12, further comprising:
    cooling a surface of the tongue while an electrode ablates an interior section of the tongue.

14. The method of claim 10, wherein the catheter is introduced into an oral cavity and one or more electrodes are introduced into an interior of the tongue through one of an inferior dorsal surface of the tongue, a dorsum surface of the tongue, or a tip of the tongue.

15. The method of claim 10, wherein the catheter is introduced into an oral cavity and one or more electrodes are introduced into an interior of the tongue through a ventral surface of the tongue.

16. The method of claim 1, further comprising:
    providing an imaging apparatus.

17. The method of claim 16, wherein the imaging apparatus is an ultrasound device.

18. The method of claim 16, further comprising:
    imaging the tongue prior to debulking the tongue.

19. The method of claim 16, further comprising:
    imaging the tongue after debulking the tongue.

20. A method for treating airway obstructions, comprising:
    providing an ablation apparatus including a source of electromagnetic energy and one or more electromagnetic energy delivery electrodes coupled to the electromagnetic energy source;
    advancing at least one electrode into an interior of a tongue;
    delivering sufficient electromagnetic energy from the electrode into the interior of the tongue to debulk an interior section without damaging a hypoglossal nerve; and
    retracting the electrode from the interior of the tongue.

21. The method of claim 20, wherein the electrode is advanced into an interior of the tongue through a ventral surface of the tongue.

22. The method of claim 20, wherein the electrode is advanced into an interior of the tongue through an inferior dorsal surface of the tongue.

23. The method of claim 20, wherein the electrode is advanced into an interior of the tongue through a dorsum surface of the tongue.

24. The method of claim 20, wherein the electrode is advanced into an interior of the tongue through a tip of the tongue.

25. The method of claim 20, wherein the ablation apparatus further comprises:
    a catheter including a lumen, wherein the electrode is deployed from the catheter lumen into an interior of the tongue.

26. The method of claim 25, wherein the catheter is introduced into an oral cavity and one or more electrodes are introduced into an interior of the tongue through one of an inferior dorsal surface of the tongue, a dorsum surface of the tongue, or a tip of the tongue.

27. The method of claim 25, wherein the catheter is introduced into an oral cavity and one or more electrodes are introduced into an interior of the tongue through a ventral surface of the tongue.

28. The method of claim 20, wherein the energy source is an RF source.

29. The method of claim 20, wherein the tongue is debulked sufficiently to increase a cross-sectional area of the airway passage.

30. The method of claim 20, further comprising:
providing an imaging apparatus.

31. The method of claim 30, further comprising:
imaging the tongue prior to debulking.

32. The method of claim 30, further comprising:
imaging the tongue after debulking.

33. A method for treating airway obstructions, comprising:
providing an ablation apparatus including a source of electromagnetic energy and one or more electromagnetic energy delivery electrodes coupled to the electromagnetic energy source;
advancing at least one electrode into a lingual tonsil;
delivering sufficient electromagnetic energy from the electrode into an interior of the lingual tonsil and debulk the lingual tonsil; and
retracting the electrode from the lingual tonsil.

34. The method of claim 33, wherein the energy source is an RF source.

35. The method of claim 33, wherein one or more electrodes are advanced into a different section of the lingual tonsil.

36. The method of claim 33, further comprising:
providing an imaging apparatus.

37. The method of claim 36, wherein the imaging apparatus is an ultrasound device.

38. The method of claim 36, further comprising:
imaging the lingual tonsil prior to debulking.

39. The method of claim 36, further comprising:
imaging the lingual tonsil after debulking.

40. A method for reducing a volume of a tongue, comprising:
providing an ablation apparatus including one or more RF electrodes coupled to an RF energy source;
positioning at least one electrode into an interior of the tongue;
delivering RF energy from the electrode into the interior of the tongue; and
ablating a section in the interior of the tongue without damaging a hypoglossal nerve.

41. A method for treating airway obstructions, comprising:
providing an ablation apparatus including one or more RF electrodes coupled to an RF energy source;
positioning at least one electrode into an interior of a tongue;
delivering RF energy from the electrode into the interior of the tongue; and
creating cell necrosis in the interior of the tongue without damaging a hypoglossal nerve.

42. A method for treating airway obstructions, comprising:
providing an ablation apparatus including one or more RF electrodes coupled to an RF energy;
positioning at least one electrode into an interior of a lingual tonsil;
delivering sufficient RF energy from the electrode into an interior of the lingual tonsil;
creating cell necrosis in the interior of the lingual tonsil.

* * * * *